United States Patent [19]

Takahashi et al.

[11] Patent Number: 5,071,249
[45] Date of Patent: Dec. 10, 1991

[54] LIGHT WAVEFORM MEASURING APPARATUS

[75] Inventors: Akira Takahashi; Musubu Koishi; Yutaka Tsuchiya, all of Hamamatsu, Japan

[73] Assignee: Hamamatsu Photonics K.K., Shizuoka, Japan

[21] Appl. No.: 416,774

[22] Filed: Oct. 4, 1989

[30] Foreign Application Priority Data

Oct. 5, 1988 [JP] Japan ............................... 63-251517
Mar. 8, 1989 [JP] Japan ................................. 1-55531

[51] Int. Cl.⁵ .......................... G01J 3/30; F21V 9/16
[52] U.S. Cl. ................................. 356/318; 250/458.1
[58] Field of Search .................... 356/317, 318, 417; 250/458.1, 459.1, 461.1, 461.2, 365; 307/427

[56] References Cited

U.S. PATENT DOCUMENTS 4,959,665 8/1989 Saito et al. ......................... 307/427

OTHER PUBLICATIONS

Stavola et al., "Picosecond Time Delay Fluorimetry Using Jitter-Free Streak Camera," Optic Communications, 9/19/80, vol. 34, #3, pp. 404-408.
Yamazaki et al., "Microchannel-Plate Photomultiplier Applicability to the Time-Correlated Photon Counting Method," Rev. Sci. Instrum, 56(6), pp. 1187-1194, (Jun. 1985).
Sumitani et al., "Channel-Three Decay in Benzene: A Picosecond Flourescence Investigation", Chemical Physics 93, pp. 359-371, 1985.
Taniuchi et al., "Second Harmonic Generation by Cherenkov Radiation in Proton-Exchanged $LiNbO_3$ Optical Waveguide", Technical Digest CLEO, pp. 230-231, 1986.
Technical Note: Measurement by OOS-01/VIS, Hamamatsu, pp. 1-16, Nov. 1988.
Technical Note: Application Example of PLP-01, Hamamatsu, Catalog No.: TV-169, Jan. 1989.
Absolute Two Photon Fluorescence with Low Power CW Lasers, Catalano et al., American Institute of Physics, Applied Physics Letter, 5/81, pp. 745-747.

*Primary Examiner*—F. L. Evans
*Assistant Examiner*—K. P. Hantis
*Attorney, Agent, or Firm*—Finnegan, Henderson, Farabow, Garrett, and Dunner

[57] ABSTRACT

A wavelength of light emitted from a semiconductor laser is shifted to a shorter wavelength with wavelength converting means and the resulting light of a shorter wavelength is applied to a sample. Upon exposure to the light of the shorter wavelength, the sample emits light of interest and its waveform is measured with measuring means. Fundamental wavelength laser light which passes through the waveform converting means is outputted therefrom in synchronism with the light of a shorter wavelength and detected by a first photodetector. The waveform of the light of interest can be measured correctly on the basis of an output signal from the first photodetector.

4 Claims, 5 Drawing Sheets

LIGHT WAVEFORM MEASURING APPARATUS

BACKGROUND OF THE INVENTION

The present invention relates to an apparatus for measuring the waveform of light emitted from a sample upon exposure to a laser beam.

While various types of apparatuses are available for measuring the waveform of light emitted from a sample upon exposure to a laser beam, it is known that the life of fluorescence can be measured by a time-correlation-single-photon-counting method. To briefly describe the time-correlation-single-photon-counting method, a light pulse of a satisfactorily short duration is applied to the sample and the fluorescence photon emitted from the sample upon exposure is detected, thereby measuring the time from the application of the light pulse to the detection of fluorescence photon. The photon detection is adjusted so that no more than a single photon is detected upon one application of light pulse. This time measurement is repeated a number of times (as many as a million times if precise results are required) and the many sets of data obtained are represented in a histogram to determine the life characteristics of fluorescence from the sample (light waveform).

Light waveform measuring apparatuses, including the above fluorescence life measuring apparatus comprise a light source and a photodetector to measure various light waveforms such as the fluorescence life curve. While flash lamps and gas lasers have been used conventionally as such a light source for those light waveform measuring apparatuses, recently small and easy-to-handle semiconductor lasers are used.

The semiconductor lasers commercially available today operate at wavelengths longer than 600 nm and if it is desired to irradiate samples with light pulses having a shorter wavelength, gas lasers and other conventional lasers have to be used with large setups. Thus, exposing samples to light pulses of short wavelengths has suffered from the problem of increased equipment size.

SUMMARY OF THE INVENTION

An object, therefore, of the present invention is to solve the aforementioned problem of the prior art by a novel apparatus for measuring light waveforms. The novel apparatus uses a semiconductor as a pulse light source and shifts the wavelength of the output laser light to the shorter wavelength with wavelength converting means so that the sample can be exposed to light of shorter wavelength. Further, in order to insure that the intensity of exposing light will not become unduly low, the apparatus of the present invention includes a first photodetector that detects laser light of the fundamental wave which is transmitted from the wavelength converting means unaffected and measuring means which measures the waveform of light of interest from the sample on the basis of the output from the first photodetector.

In the apparatus having the construction described above, the wavelength of light emitted from the semiconductor laser is shifted to the shorter wavelength with the wavelength converting means and the resulting light of shorter wavelength is applied to the sample. Upon exposure to the light of shorter wavelength, the sample emits the light of interest and its wavelength is measured with the measuring means. Laser light of the fundamental wave which is transmitted from the wavelength converting means is produced therefrom in synchronism with the light of shorter wavelength and detected by the first photodetector. The waveform of the light of interest can be measured correctly on the basis of the detection output from the first photodetector.

DETAILED DESCRIPTION OF THE PREFERRED EMBODIMENTS

Figure 1:
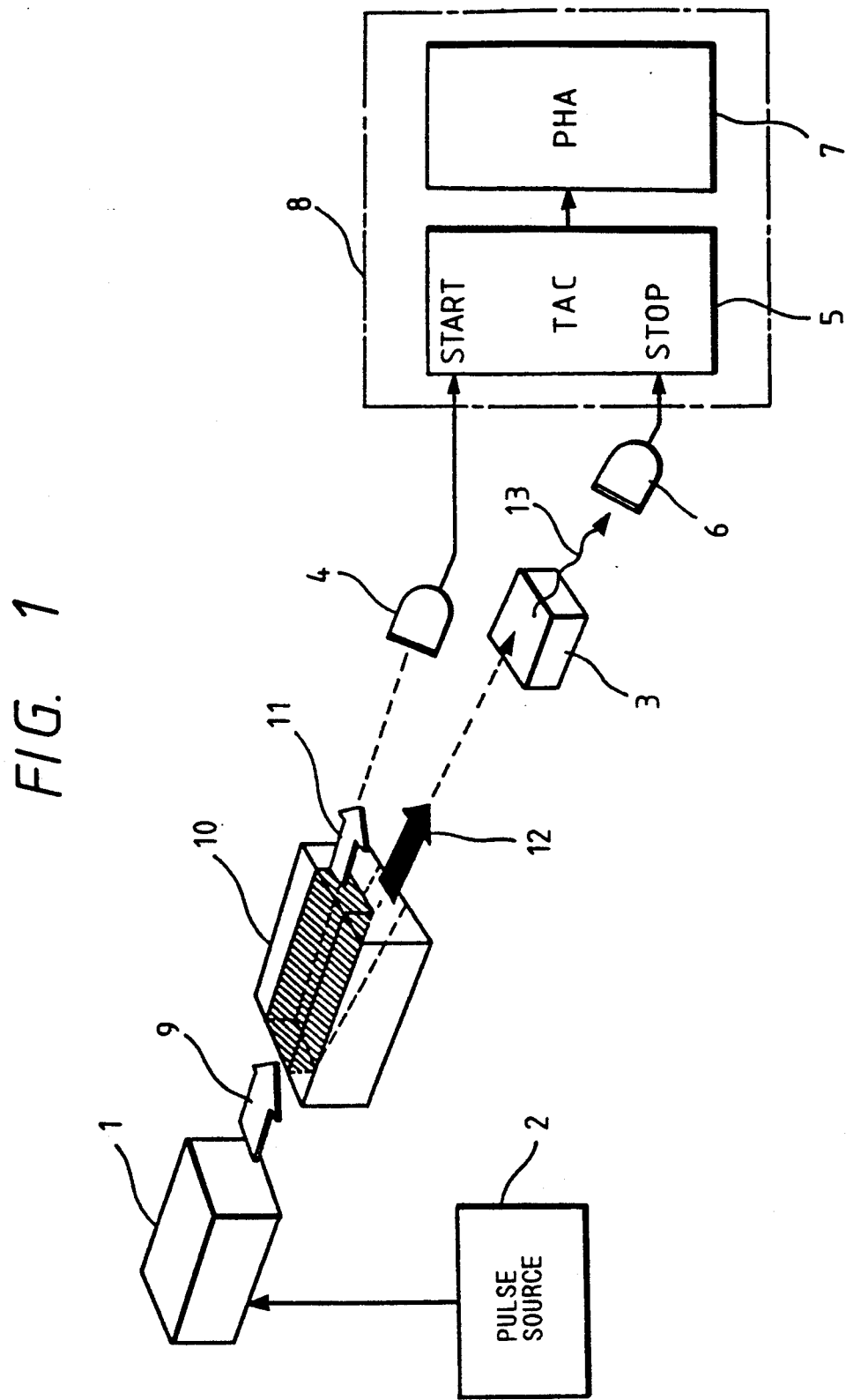
FIG. 1 is a block diagram of a light waveform measuring apparatus according to an embodiment of the present invention.

FIG. 1 is a block diagram showing a light wavelength measuring apparatus according to an embodiment of the present invention. A semiconductor laser (laser diode) 1 is excited by rapid rising current pulses from a pulse source 2 to produce pulsed laser light 9 composed of pulses of a satisfactorily short duration (<1 ns). In the embodiment shown in FIG. 1, red laser light having a wavelength of 820 nm is produced from the semiconductor laser 1 and launched into wavelength converting means 10. The wavelength converting means 10 is formed of an optical crystalline material having a non-linear optical effect (e.g. lithium niobate, $LiNbO_3$) and produces blue light of a second harmonic wave 12, which is laser light having a wavelength of 410 nm, one half that of the incident laser light 9. On an extension of the axis of the second harmonic wave light 12, a sample 3 is located and emits fluorescent light upon receiving the second harmonic wave light 12 from the wavelength converting means 10.

As described above, the laser light whose wavelength has been shifted to the shorter wavelength by the wavelength converting means 10 is applied to the sample 3 to excite it in the apparatus of the present invention. This permits the use of small and easy-to-handle semiconductor laser 1 as a light source while the sample 3 is irradiated with laser light having the short wavelength that has been unattainable with semiconductor lasers in the prior art.

For successful performance of the time-correlation-single-photon-counting method, it is necessary that the duration of time from the application of a light pulse to the detection of a fluorescence photon be measured correctly. To meet this requirement, a measurement start signal which serves as a reference for starting the time measurement must be obtained for each application of light pulse. The method that has been used in the prior art to obtain this measurement start signal comprises splitting the irradiating light pulse into two beamlets by a suitable means such as a half mirror, detecting one of the beamlets with a suitable device such as a photodetector, and using the detection output as the measurement start signal. The use of a half mirror involves the disadvantage of necessitating an optical setting up operation. However, if an electric pulse for driving a pulse light source is directly used as the measurement start signal, drifts will occur on account of such factors as changes in the temperature of the pulse source, making it impossible to maintain a constant time interval between the actual application of a light pulse and the issuance of the measurement start signal. To avoid this problem, a half mirror has had to be used to obtain the measurement start signal.

However, the light intensity of the second harmonic wave 12 produced from the wavelength converting means 10 is very low and only 1-2% of the intensity of the incident laser light 9. Therefore, if the second harmonic wave 12 which is a light pulse to be applied to the sample 3 is split by means of a half mirror to obtain the measurement start signal, the intensity of not only the irradiating light falling on the sample 3 but also the beamlet for obtaining the measurement start signal will become very low.

To deal with this problem, the apparatus of the present invention uses the fundamental wave 11 from the wavelength converting means 10 to obtain the measurement start signal for the following two reason. First, the fundamental wave 11 is transmitted from the wavelength converting means 10 and is produced, therefrom in synchronism with the second harmonic wave 12. Second it has a high light intensity. Stated more specifically, a first photodetector 4, composed of a photodiode or like device, is located on an extension of the axis of the fundamental wave light 11 delivered from the wavelength converting means 10, and the resulting detection output is fed as the measurement start signal to the START terminal of a time-to-amplitude converter (TAC) 5.

When the second harmonic wave 12 emitted from the wavelength converting means 10 is launched into the sample 3, the latter will emit fluorescence photons 13 which are detected by a second photodetector 6 typically made of a photomultiplier tube. The detection output of this photodetector 6 is fed to the STOP terminal of TAC 5. The photodetector 6 is set for such a condition that it will detect only, one photon 13 after the sample 3 has been subjected to application of several tens of light pulses.

TAC 5 is a device that outputs a voltage pulse having a height proportional to the time difference between the signal fed at the START terminal and the signal fed at the STOP terminal. Thus, aside from the actual lag due to the propagation times of laser light and the detection output, the output voltage pulse has a height corresponding to the time between the application of a light pulse from the semiconductor laser 1 and the emission of a fluorescence photon from the sample 3. As already mentioned, the second photodetector 6 is set to operate under such a condition that it detects one photon 13 upon application of several tens of optical pulses, so TAC 5 will produce its output voltage pulse only once when it receives several tens of measurement start signals.

The output terminal of TAC 5 is connected to the input terminal of a pulse height analyzer (PHA) 7. PHA 7 stores the height of each input voltage pulse in a digitized form and counts the number of input pulses according to their height. This analyzer combines with TAC 5 to make up means 8 for computing the life characteristics of fluorescence.

Figure 2:
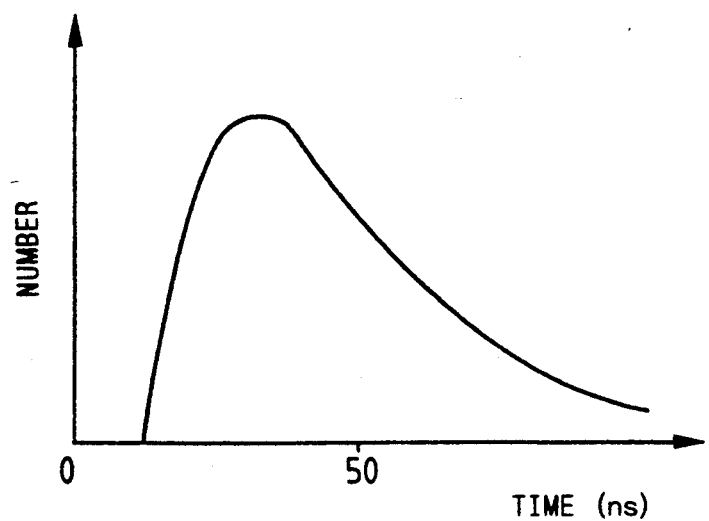
FIG. 2 is a graph showing the results of computation with PHA 7 shown FIG. 1.

FIG. 2 is a graph illustrating the results of counting which is conducted with PHA 7 when it receives multiple voltage pulses from TAC 5. The horizontal axis of the graph plots the time in proportion t the height of voltage pulse and the vertical axis plots the number of voltage pulses. The vertical axis shows the probability that a photon 13 will be detected at a certain time and its value is proportional to the intensity of the fluorescent light at that time. Hence, the graph is a direct presentation of the time profile of the intensity of fluorescent light, or life characteristics of fluorescence. In practice, from a million to several tens of millions of light pulses are applied and measurements are continued until about a million photons have been detected and the life characteristics of fluorescence are computed on the basis of the results of the measurements.

Figure 3:
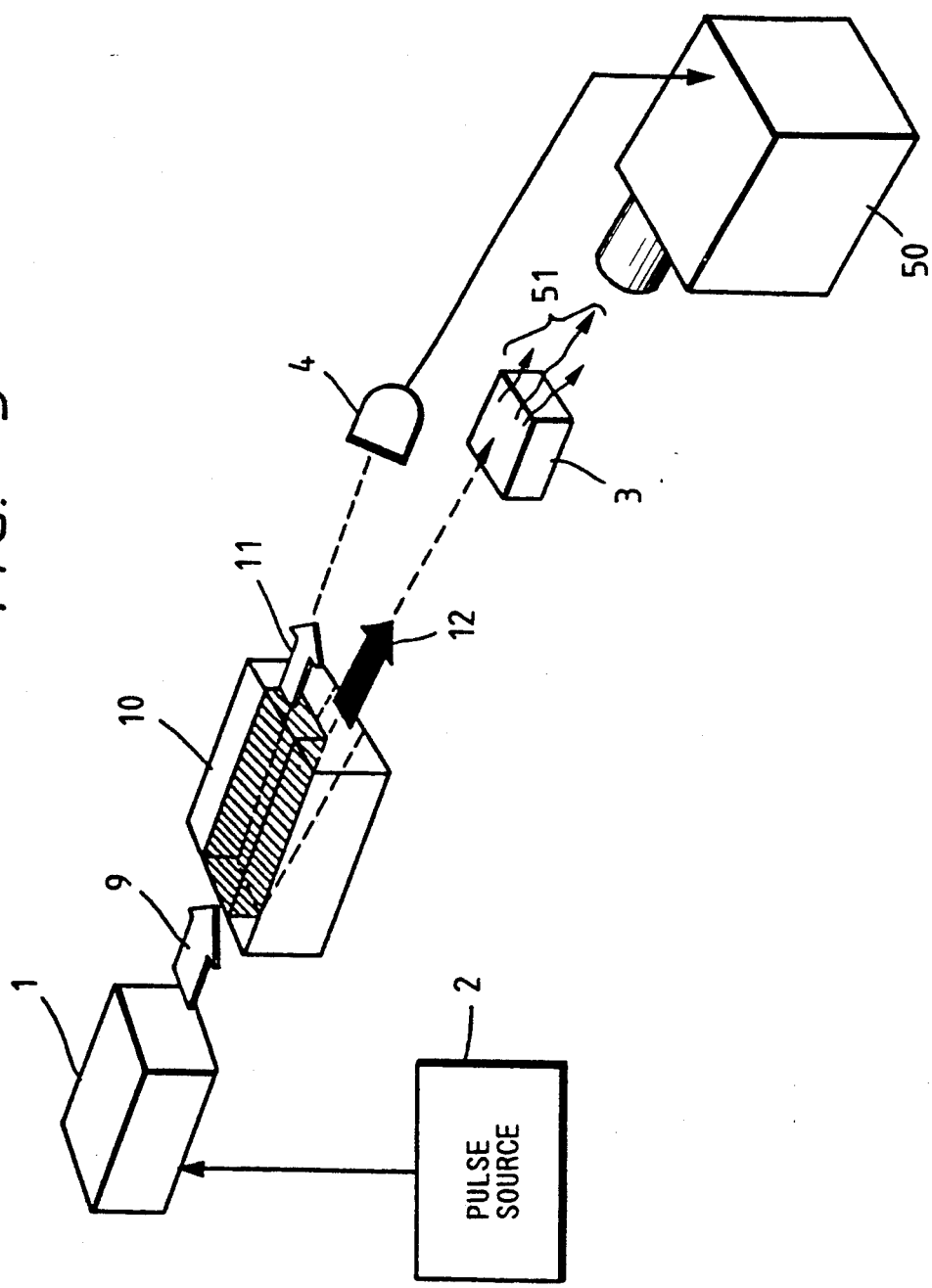
FIG. 3 is a block diagram of a light waveform measuring apparatus according to another embodiment of the present invention.

FIG. 3 is a block diagram of a light waveform measuring apparatus according to another embodiment of the present invention. The components which are the same as those shown in FIG. 1 are identified by like numerals and will not be described in detail. In this embodiment, a streak camera 50 is used in place of TAC 5, PHA 7 and photodetector 6. The construction of this streak camera and its operation are described with reference to FIG. 4 As shown, the streak camera generally indicated by 50 consists basically of a streak tube 52 and a camera 53 taking the streak image produced with the streak tube 52. Light 51 that is emitted from the sample and is to be measured with the streak camera passes through an input optical system including a slit (not shown) and lenses (also not shown) and reaches a photocathode 55 of the streak tube 52, where it is converted to electrons. The resulting photoelectrons are accelerated by means of an accelerating electrode 56 and guided between deflecting plates 57 toward a microchannel plate (MCP) 58. As they pass between the deflecting plates 57, the photoelectrons are swept by the sweep voltage applied between the deflecting plates 57 and arrive at the MCP 58. The photoelectrons are multiplied at the MCP 58 by a sufficient factor and excite a phosphor screen 60 for forming a streak image. The streak image is taken with the camera 53 placed behind the phosphor screen 60. The sweep voltage must be applied to the deflecting plates 57 in synchronism with the passages of photoelectrons between those plates. To this end, the streak camera 50 is supplied with the detection output of the first photodetector 4 as a trigger signal for starting the sweep operation and in response to this trigger input, a sweep voltage generator 62 generates the sweep voltage which is applied to the deflecting plates 57.

When the second harmonic wave 12 from the wavelength converting means 10 is launched into the sample 3, the latter emits light 51 to be measured. This light 51 is launched into the streak camera 50 which produces a streak image that visualizes the waveform, or temporal change of intensity, of the light 51 emitted from the sample 3.

The measurement described above is repeated and the resulting streak images are integrated with a suitable apparatus such as an image processor (not shown) to reconstruct a streak image having a high signal-to-noise ratio (S/N ratio), or the accurate waveform of the light of interest.

Figure 4:
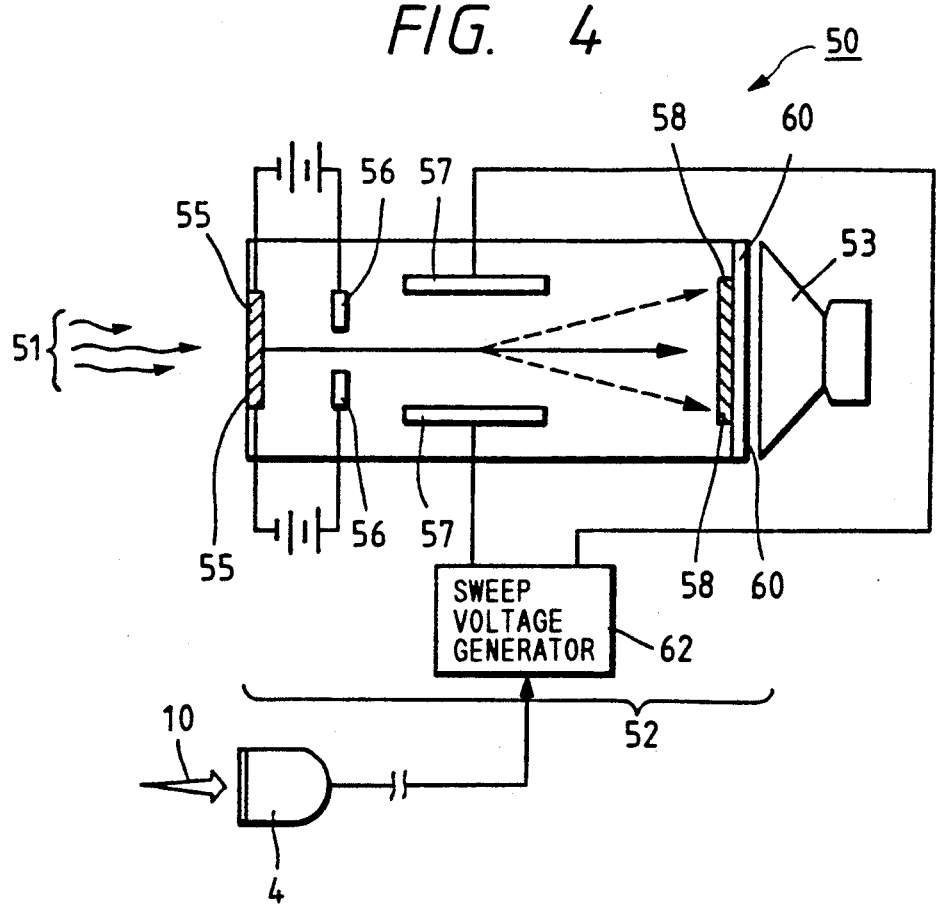
FIG. 4 is a schematic view showing the construction of a streak camera.

The streak camera 50 shown in FIGS. 3 and 4 may be replaced by light waveform observing means of the sampling type. An exemplary construction of this light waveform observing means of the sampling type and its operation are briefly described with reference to FIG. 5. The apparatus shown in FIG. 5 consists basically of a sampling type streak tube 65 and an information processor 66 which processes the information on the waveform of light 51 obtained by extracting part of it with the streak tube. The light 51 emitted from the sample 3 and observed with the apparatus is focused with a lens 67 on a photocathode 68 of the streak tube 65. The incident light on the photocathode 68 is converted to electrons the number of which is proportional to the intensity of light. The resulting photoelectrons are accelerated by an accelerating electrode 70 and guided between deflecting plates 71 to reach a slit plate 72. As they pass between the deflecting plates 71, the photoelectrons are swept by the sweep voltage applied between the plates 71 and arrive at the slit plate 72. Since a tiny slit perpendicular to the sweep direction is formed in the plate 72, only part of the electrons can pass through the plate to reach a phosphor screen 73 behind it. The phosphor screen 73 emits light upon excitation by the impinging electrons. The intensity of emitted light is sensed by a photomultiplier tube 75 and amplified by an amplifier 76 to produce an output electric signal. The signal thus obtained by sampling the intensity of light 51 is stored in the information processor 66.

Figure 6:
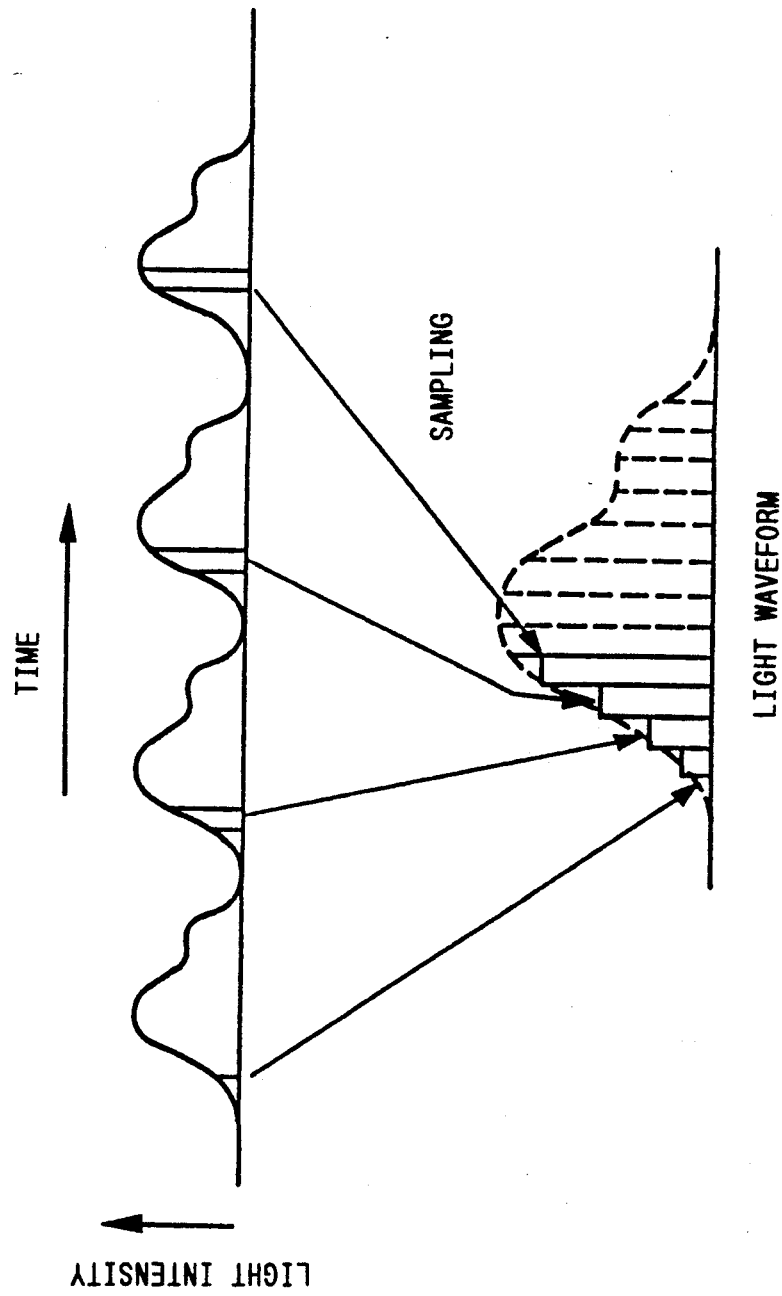
FIG. 6 is a diagram explaining how a light waveform is obtained with the light waveform observing means of the sampling type.

The sampling operation described above is repeated with the timing of each sweep being delayed by small but increasing amounts from the incidence of light 51 and the information obtained is processed to obtain a light waveform as depicted in FIG. 6.

Figure 5:
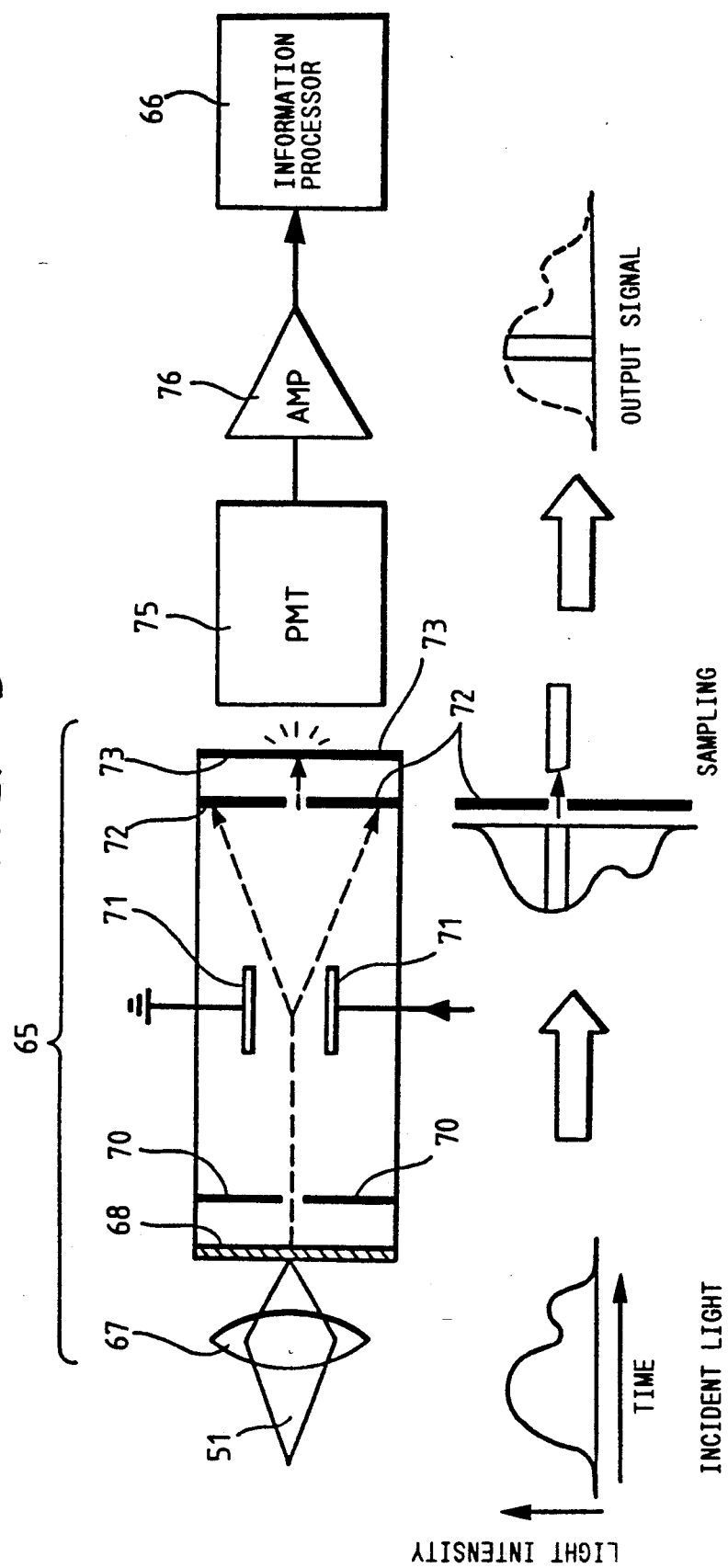
FIG. 5 is a schematic view showing the construction of light waveform observing means of the sampling type.

In the apparatus shown in FIG. 5, the detection output of the first photodetector 4 is fed to the sampling type streak tube 65 and each application of sweep voltage to the deflecting plates 71 is delayed progressively from the time at which the detection output of the first photodetector 4 is fed to the streak tube 65.

As described on the foregoing pages, the light waveform measuring apparatus of the present invention uses wavelength converting means to create laser light of a shorter wavelength with which the sample is to be excited. Further, laser light of the fundamental wave that is transmitted from the wavelength converting means is detected and the waveform of light of interest is measured on the basis of the resulting detection output. Hence, the apparatus of the present invention is capable of precisely obtaining irradiation times of light pulses without reducing the intensity of laser light being emitted from the wavelength converting means to be launched into the sample.

What is claimed is:

1. A light waveform measuring apparatus for measuring a waveform of light emitted from a sample upon exposure to laser light, comprising:
   a semiconductor laser for emitting first laser light having a fundamental wavelength;
   wavelength converting means for emitting, in response to substantially all of said first laser light, second laser light having a wavelength shorter than said fundamental wavelength, and a third laser light having said fundamental wavelength, said second laser light irradiating said sample;
   a first photodetector for detecting said third laser light transmitted from said wavelength converting means, and for producing a first output signal; and
   measuring means for detecting said light emitted from said sample to measure said waveform thereof on the basis of said first output signal from said first photodetector.

2. The apparatus according to claim 1, wherein said measuring means comprises a streak camera which performs a sweeping operation on the basis of said first output signal from said first photodetector.

3. The apparatus according to claim 1, wherein said measuring means comprises light waveform observing means of sampling type which operates on the basis of said first output signal from said first photodetector.

4. The apparatus according to claim 1, wherein said measuring means comprises:
   a second photodetector for detecting photons of said light emitted from said sample and for producing a second output signal; and
   means for performing a plurality of measurements of time between said first output signal from said first photodetector and said second output signal from said second photodetector, and for measuring said waveform of said light by a time-correlation-single-photon-counting method.

* * * * *